US011767345B2

United States Patent
Yoshida et al.

(10) Patent No.: US 11,767,345 B2
(45) Date of Patent: Sep. 26, 2023

(54) ANTIVIRAL PEPTIDE AND USE THEREOF

(71) Applicants: TOAGOSEI CO., LTD., Tokyo (JP); NATIONAL UNIVERSITY CORPORATION HOKKAIDO UNIVERSITY, Sapporo (JP)

(72) Inventors: Tetsuhiko Yoshida, Tsukuba (JP); Ayato Takada, Sapporo (JP); Nahoko Baileykobayashi, Tsukuba (JP)

(73) Assignees: TOAGOSEI CO., LTD, Tokyo (JP); National University Corporation Hokkaido University, Hokkaido (JP)

( * ) Notice: Subject to any disclaimer, the term of this patent is extended or adjusted under 35 U.S.C. 154(b) by 34 days.

(21) Appl. No.: 17/329,418

(22) Filed: May 25, 2021

(65) Prior Publication Data
US 2021/0380642 A1 Dec. 9, 2021

(30) Foreign Application Priority Data
Jun. 4, 2020 (JP) ................................. 2020-097427

(51) Int. Cl.
C07K 14/00 (2006.01)
C07K 14/005 (2006.01)
A61K 38/00 (2006.01)
A61P 31/12 (2006.01)

(52) U.S. Cl.
CPC ............ *C07K 14/001* (2013.01); *A61K 38/00* (2013.01); *C07K 2319/10* (2013.01)

(58) Field of Classification Search
CPC .............. C07K 14/001; C07K 2319/10; C07K 14/005; A61K 38/00; A61P 31/12
See application file for complete search history.

(56) References Cited

U.S. PATENT DOCUMENTS

| 2009/0012000 | A1 | 1/2009 | Yoshida et al. | |
| 2009/0258815 | A1 | 10/2009 | Yoshida et al. | |
| 2012/0201846 | A1* | 8/2012 | Rehm | A61P 31/12 435/69.3 |
| 2016/0326488 | A1* | 11/2016 | Tanaka | C12N 5/067 |
| 2017/0065702 | A1* | 3/2017 | Berry | G01N 33/56983 |
| 2018/0022790 | A1* | 1/2018 | Holtsberg | A61K 39/395 424/139.1 |
| 2019/0290745 | A1* | 9/2019 | Robinson | A61P 37/04 |

FOREIGN PATENT DOCUMENTS

| JP | 2007230903 A | 9/2007 |
| JP | 2007230904 A | 9/2007 |

OTHER PUBLICATIONS

Definition of dispose of from dictionary.com, pp. 1-3. Accessed Feb. 22, 2023. (Year: 2023).*
Yampolsky et al., "The Exchangeability of Amino Acids in Proteins," Genetics, 2005, 170: 1459-1472. (Year: 2005).*
Liao et al., "Removal of N-terminal methionine from recombinant proteins by engineered *E. coli* methionine aminopeptidase," Protein Science, 2004, 13: 1802-1810. (Year: 2004).*
Marin-Navarro et al., "Identification and Structural Analysis of Amino Acid Substitutions that Increase the Stability and Activity of Aspergillus niger Glucose Oxidase," PLOS One, Dec. 7, 2015, 1-14. (Year: 2015).*
Saller et al., "Molecular ensembles make evolution unpredictable," PNAS, 2017, 114(45): 11938-11943. (Year: 2017).*
Ayato Takada et al., "A system for functional analysis of Ebola virus glycoprotein," Proc. Natl. Acad. Sci. USA, vol. 94, pp. 14764-14769, Dec. 1997.
Ayato Takada et al., "Identification of Protective Epitopes on Ebola Virus Glycoprotein at the Single Amino Acid Level by Using Recombinant Vesicular Stomatitis Viruses," Journal of Virology, vol. 77, No. 2, pp. 1069-1074, Jan. 2003.
Eri Nakayama et al., "Antibody-Dependent Enhancement of Marburg Virus Infection," The Journal of Infectious Disease, vol. 204, pp. S978-S985, 2011.

* cited by examiner

*Primary Examiner* — Julie Ha
(74) *Attorney, Agent, or Firm* — Occhiuti & Rohlicek LLP

(57) ABSTRACT

The synthetic peptide disclosed here includes (1) an amino acid sequence represented by any of SEQ ID NOS:1 to 10, or a modified amino sequence formed by deletion, substitution or addition of 1, 2 or 3 amino acid residues in any of these amino acid sequences, together with (2) an amino acid sequence (CPP sequence) that functions as a cell penetrating peptide (CPP), and consists of a total of not more than 100 amino acid residues.

2 Claims, 3 Drawing Sheets

Specification includes a Sequence Listing.

ANTIVIRAL PEPTIDE AND USE THEREOF

CROSS-REFERENCE TO RELATED APPLICATIONS

The priority claim for this application is based on Japanese Patent Application No. 2020-097427 submitted on Jun. 4, 2020, and the entire contents of that Japanese Patent Application are herein incorporated by reference.

TECHNICAL FIELD

The present invention relates to an artificially synthesized antiviral peptide having antiviral properties against at least one kind of virus, and to a use thereof. It also relates to the use of a synthetic peptide including an amino acid sequence represented by any of SEQ ID NOS:1 to 10 together with a cell penetrating peptide sequence.

TECHNICAL BACKGROUND

Due to the current lack of effective preventative and antiviral agents, there are many viral diseases for which treatment is limited to symptomatic treatment. Even if an effective antiviral agent exists, the virus may acquire drug resistance, and in some cases existing treatments are not an option and adequate treatment is not possible. Therefore, research and development of antiviral agents with different mechanisms of action and chemical properties is being actively pursued in the treatment of viral diseases. As shown in Japanese Patent Application Publication No. 2007-230904 and Japanese Patent Application Publication No. 2007-230903 and the like, one approach to this has been to develop naturally occurring and artificially produced antiviral peptides capable of arresting or suppressing viral infection and proliferation.

The family Filoviridae includes the Ebolavirus and Marburgvirus genera, and certain viruses belonging to these genera exhibit extremely high rates of infection and mortality in primates including human. So far, natural outbreaks of such viruses have been limited to certain regions. As global transportation networks continue to expand, however, these viruses are becoming a subject of concern as pathogens that can cause imported infections.

SUMMARY OF THE INVENTION

There are thus far no effective preventative or therapeutic agents for such viruses, and there is increasing demand for the rapid establishment of effective therapeutic methods.

It is an object of the present invention to design a peptide with a different structure from the antiviral peptides described in the above patent literature, which is a novel artificial antiviral peptide that is different from peptides that occur and function as antiviral peptides in nature. Other objects are to manufacture an antiviral peptide designed by the present invention, and to provide an antiviral composition (typically, an antiviral agent or research reagent that is a pharmaceutical composition) having this peptide as a principal component.

The inventors conducted screening to evaluate the antiviral properties of synthetic peptides having various amino acid sequences against several viruses. An amino acid sequence that exhibited the effect of suppressing viral proliferation (that is, antiviral activity) was discovered as a result of this screening of synthetic peptides, and the present invention was perfected.

The techniques disclosed here provide a synthetic peptide that suppresses the proliferation of at least one kind of virus.

This synthetic peptide includes (1) an amino acid sequence represented by any of SEQ ID NOS:1 to 10 below, or a modified amino sequence formed by deletion, substitution or addition of 1, 2 or 3 amino acid residues in these amino acid sequences, and (2) an amino acid sequence (CPP sequence) that functions as a cell penetrating peptide (CPP).

This synthetic peptide has a total of not more than 100 amino acid residues.

With a synthetic peptide of this configuration, it is possible to suppress the proliferation of at least one kind of virus.

In a preferred embodiment, the CPP sequence is a polyarginine or an amino acid sequence represented by any one of SEQ ID NOS:11 to 28. The polyarginine is not particularly limited but may be composed of from 3 to 11 arginine residues for example. Viral proliferation can be more effectively suppressed with such a configuration.

Preferably the CPP sequence is linked to the N-terminal end or C-terminal end of the amino acid sequence represented by (1) above either directly or via a linker consisting of 1 to 5 amino acid residues. This configuration is suitable for realizing the effects of the present invention.

In a preferred embodiment, the synthetic peptide disclosed here has an amino acid sequence represented by any of SEQ ID NOS:29 to 35. Viral proliferation can be suppressed more effectively with this configuration.

Also provided is an antiviral composition for suppressing the proliferation of at least one kind of virus, including any of the synthetic peptides (antiviral peptides) disclosed here together with at least one pharmacologically acceptable carrier.

Because it contains the antiviral peptide disclosed here, this composition can be used as an antiviral agent or as a research material for developing a novel antiviral agent.

Also provided is a method for suppressing the proliferation of at least one kind of virus, wherein any of the synthetic peptides (antiviral peptides) disclosed here is supplied at least once to a target cell, tissue or the like (in vitro or in vivo for example).

With the method of this configuration, the proliferation of at least one kind of virus can be arrested or suppressed by supplying the antiviral peptide disclosed here to a target.

In a preferred embodiment, the virus is a vesicular stomatitis virus or a virus having a glycoprotein of a virus belonging to the Filoviridae (hereunder also called a filovirus).

The proliferation suppressing method of this configuration can be used especially favorably when the virus that is the target of proliferation suppression is a viral species described above.

Preferably the filovirus is an Ebolavirus or Marburgvirus.

The proliferation suppressing method of this configuration can be used especially favorably when the filovirus that is the target of proliferation suppression is a viral species described above.

DESCRIPTION OF THE RELATED EMBODIMENTS

Figure 1:
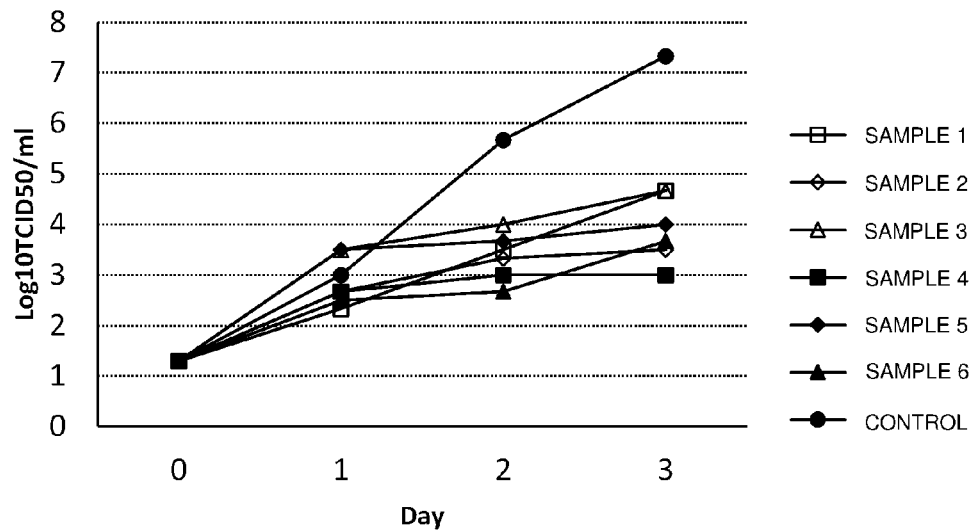
FIG. 1 is a graph showing changes over time in Example 1 in the viral load ($Log_{10}$ $TCID_{50}$/ml) in culture supernatant of Vero E6 cells that were cultured for 1, 2 and 3 days after inoculation with $10^3$ PFU of VSV-ZGP and subsequent addition of any of the sample peptides 1 to 6 to a concentration of 20 µM, or with no sample peptide added.

Preferred embodiments of the invention are explained below. Apart from matters that are specifically mentioned in this Description (such as the primary structure and chain length of the synthetic peptide disclosed here), matters necessary for the implementation of the present invention (such as peptide chemical synthesis methods, cell culture methods, and general matters related to preparing an antiviral composition containing the peptide disclosed here) can be understood by a person skilled in the art as design matters based on prior art in the fields of cellular engineering, physiology, medicine, pharmacology, organic chemistry, biochemistry, genetic engineering, protein engineering, molecular biology, genetics and the like. The present invention can be implemented based on the content disclosed in this Description and on technical common knowledge in these fields. In the following explanations, amino acids are represented by 1-letter notation (but by 3-letter notation in the sequence tables).

The entire contents of all literature cited in this Description are herein incorporated by reference.

In this Description, an "artificially synthesized peptide" is not one whose peptide chain exists stably and independently in nature by itself, but rather a peptide fragment that has been manufactured by artificial chemical synthesis or biosynthesis (production based on genetic engineering for example) and can exist stably in a particular system (such as a composition constituting an antiviral agent). The term "peptide" here refers to an amino acid polymer having multiple peptide bonds, and the number of amino acid residues contained in the peptide chain is not particularly limited, but a relatively low-molecular-weight peptide with a total of not more than 100 (or preferably not more than 80, or more preferably not more than 70, or not more than 60 for example) amino acid residues is typical.

Unless otherwise specified, the term "amino acid residue" in this Description includes the N-terminal amino acid and C-terminal amino acid of the peptide chain.

In the amino acid sequences described in this Description, the left end is normally the N-terminal end and the right end is normally the C-terminal end.

A "modified amino acid sequence" of a specific amino acid sequence in this Description is an amino acid sequence formed by substituting, deleting or adding (inserting) one or more (typically not more than 9, or preferably not more than 5) amino acid residues, such as 1, 2 or 3 amino acid residues in the specific amino acid sequence without detracting from the function (also called "viral proliferation suppression") of that sequence. Typical examples of modified amino acid sequences as defined in this Description include sequences produced by so-called conservative amino acid replacement in which 1, 2 or 3 amino acids are substituted conservatively (for example, by substituting a basic amino acid for another basic amino acid, such as by mutual substitution of a lysine residue and an arginine residue), and sequences produced by addition (insertion) or deletion of 1, 2 or 3 amino acid residues in the original amino acid sequence.

Consequently, specific examples of the antiviral peptide disclosed here include not only synthetic peptides consisting of amino acid sequences identical to the amino acid sequences of the sequence ID numbers given below, but also synthetic peptides consisting of modified amino acid sequences that have been obtained by substitution (typically conservative substitution), deletion or addition of 1, 2 or 3 amino acid residues in the amino acid sequences of these sequence ID numbers, and that have equivalent antiviral activity to the amino acid sequences of the sequence ID numbers.

The artificially synthesized antiviral peptide disclosed here is a short-chain peptide that does not exist in nature, namely a peptide characterized by having the following two amino acid sequences:

(1) an amino acid sequence represented by any of SEQ ID NOS:1 to 10, or an amino acid sequence formed by deleting, substituting or adding 1, 2 or 3 amino acid residues in that amino acid sequence; and (2) an amino acid sequence (CPP sequence) that functions as a cell penetrating peptide (CPP).

An amino acid sequence represented by any of SEQ ID NOS:1 to 10 is preferred as the amino acid sequence of (1).

The amino acid sequence of SEQ ID NO:1 is an amino acid sequence constituting a transmembrane region consisting of a total of 21 amino acid residues contained in a glycoprotein of one kind of isolated Lake Victoria Marburgvirus (UniProtKB-Q1PD50). Hereunder, "an amino acid sequence constituting a transmembrane region" is also termed a "TM sequence." Hereunder, "Lake Victoria Marburgvirus" is also termed a "Marburgvirus (Angola)."

The amino acid sequence of SEQ ID NO:2 is a TM sequence consisting of a total of 21 amino acid residues contained in a glycoprotein of Sudan ebolavirus (UniProtKB-Q66798). Hereunder, "Sudan ebolavirus" is also termed a "Ebolavirus (Sudan)."

The amino acid sequence of SEQ ID NO:3 is a TM sequence consisting of a total of 21 amino acid residues contained in a glycoprotein of Zaire ebolavirus (UniProtKB-Q05320). Hereunder, "Zaire ebolavirus" is also termed a "Ebolavirus (Zaire)."

The amino acid sequence of SEQ ID NO:4 is an amino acid sequence consisting of a total of 27 amino acid residues including a TM sequence (SEQ ID NO:1) contained in a glycoprotein of Marburgvirus (Angola) (UniProtKB-Q1PD50).

The amino acid sequence of SEQ ID NO:5 is an amino acid sequence consisting of a total of 27 amino acid residues including a TM sequence (SEQ ID NO:2) contained in a glycoprotein of Ebolavirus (Sudan) (UniProtKB-Q66798).

The amino acid sequence of SEQ ID NO:6 is an amino acid sequence consisting of a total of 27 amino acid residues including a TM sequence (SEQ ID NO:3) contained in a glycoprotein of Ebolavirus (Zaire) (UniProtKB-Q05320).

The amino acid sequence of SEQ ID NO:7 is a signal sequence consisting of a total of 32 amino acid residues contained in a glycoprotein of Ebolavirus (Zaire) (UniProtKB-Q05320).

The amino acid sequence of SEQ ID NO:8 is a signal sequence consisting of a total of 32 amino acid residues contained in a glycoprotein of Ebolavirus (Sudan) (UniProtKB-Q66798).

The amino acid sequence of SEQ ID NO:9 is a signal sequence consisting of a total of 18 amino acid residues contained in a glycoprotein of Marburgvirus (Angola) (UniProtKB-Q1PD50).

The amino acid sequence of SEQ ID NO:10 is a signal sequence consisting of a total of 18 amino acid residues contained in a glycoprotein of Marburg Marburgvirus (Genbank-AAR85456.1). Hereunder, "Marburg Marburgvirus" is also termed a "Marburgvirus (Marburg)."

Various conventional known CPPs may be used for the amino acid sequence of (2). For example, a so-called polyarginine consisting of at least 3 or preferably at least 5 and not more than 11 or preferably not more than 9 arginine residues (in which Rn, or n here, is an integer from 3 to 11) is desirable as the CPP used here. Apart from this, a variety of known CPPs may be adopted.

Desirable examples of CPPs are represented by SEQ ID NOS:11 to 28, but these examples are not limiting. Specifically, these are as follows.

The amino acid sequence of SEQ ID NO:11 corresponds to a NoLS (nucleolar localization signal) consisting of a total of 14 amino acid residues derived from FGF2 (basic fibroblast growth factor).

The amino acid sequence of SEQ ID NO:12 corresponds to a NoLS consisting of a total of 19 amino acid residues derived from one kind of nucleolus protein (ApLLP).

The amino acid sequence of SEQ ID NO:13 corresponds to a NoLS consisting of a total of 16 amino acid residues derived from an HSV-1 (Herpes simplex virus type 1) protein (γ(1) 34.5).

The amino acid sequence of SEQ ID NO:14 corresponds to a NoLS consisting of a total of 19 amino acid residues derived from a HIC (human I-mfa domain-containing protein) p40 protein.

The amino acid sequence of SEQ ID NO:15 corresponds to a NoLS consisting of a total of 16 amino acid residues derived from an MEQ protein of MDV (Marek disease virus).

The amino acid sequence of SEQ ID NO:16 corresponds to a NoLS consisting of a total of 17 amino acid residues derived from Survivin-deltaEX3, a protein that suppresses apoptosis.

The amino acid sequence of SEQ ID NO:17 corresponds to a NoLS consisting of a total of 7 amino acid residues derived from the vascular growth factor Angiogenin.

The amino acid sequence of SEQ ID NO:18 corresponds to a NoLS consisting of a total of 8 amino acid residues derived from MDM2, a nuclear phosphoprotein that forms a complex with the p53 tumor suppressor protein.

The amino acid sequence of SEQ ID NO:19 corresponds to a NoLS consisting of a total of 9 amino acid residues derived from GGNNVα, a Betanodavirus protein.

The amino acid sequence of SEQ ID NO:20 corresponds to a NoLS consisting of a total of 7 amino acid residues derived from NF-κB-inducing kinase (NIK).

The amino acid sequence of SEQ ID NO:21 corresponds to a NoLS consisting of a total of 15 amino acid residues derived from Nuclear VCP-like protein.

The amino acid sequence of SEQ ID NO:22 corresponds to a NoLS consisting of a total of 18 amino acid residues derived from the nucleolus protein p120.

The amino acid sequence of SEQ ID NO:23 corresponds to a NoLS consisting of a total of 14 amino acid residues derived from the ORF57 protein of HVS (Herpes virus saimiri).

The amino acid sequence of SEQ ID NO:24 corresponds to a NoLS consisting of a total of 13 amino acid residues from the $491^{st}$ amino acid residue to the $503^{rd}$ amino acid residue of LIM Kinase 2, a kind of protein kinase involved in intracellular signal transduction that is present in human endothelial cells.

The amino acid sequence of SEQ ID NO:25 corresponds to a NoLS consisting of a total of 8 amino acid residues contained in the N protein (nucleocapsid protein) of IBV (avian infectious bronchitis virus).

The amino acid sequence of SEQ ID NO:26 corresponds to a membrane penetrating motif consisting of a total sequence of 9 amino acids derived from a protein transfer domain contained in the TAT of HIV (Human Immunodeficiency Virus).

The amino acid sequence of SEQ ID NO:27 corresponds to a membrane penetrating motif consisting of a total sequence of 11 amino acids of a protein transfer domain (PTD4) obtained by modifying the above TAT.

The amino acid sequence of SEQ ID NO:28 corresponds to a membrane penetrating motif consisting of a total sequence of 18 amino acids derived from an ANT gene of Antennapedia, a mutant form of *Drosophila*.

Of these, an amino acid sequence associated with a NoLS or TAT (or a modified amino acid sequence thereof) is especially desirable. For example, the NoLS-associated CPP sequences represented by SEQ ID NO:24 and SEQ ID NO:25 and the TAT- and ANT-associated CPP sequences represented by SEQ ID NOS:26 to 28 can be used favorably for constructing the antiviral peptide disclosed here.

Information about the amino acid sequence of (1) above and the amino acid sequence of (2) above can be readily obtained by accessing the databases of various known international organizations. Examples of such databases include the database (UniProtKB) of the Universal Protein Resource (UniProt) and the database (Genbank) of the National Center for Biotechnology Information (NCBI).

As long as the peptide chain (amino acid sequence) of the antiviral peptide disclosed here includes an amino acid sequence of (1) above (hereunder generally called "amino acid sequence (1)") and an amino acid sequence of (2) above (hereunder generally called "amino acid sequence (2)"), either the amino acid sequence (1) or the amino acid sequence (2) may be disposed at the N-terminal end (or C-terminal end) relative to the other.

In a specific embodiment, the amino acid sequence (1) and the amino acid sequence (2) are disposed via a linker. The linker may be a peptidic linker. Although not particularly limited, the amino acid sequence constituting the peptidic linker is preferably a flexible amino acid sequence that does not cause steric hindrance. The peptidic linker may be a linker consisting of an amino acid sequence of not more than 10 (preferably 1 to 5, such as 1, 2, 3, 4 or 5) amino acid residues including 1 or 2 or more amino acid residues selected from lysine, alanine, glycine and the like. The peptidic linker is an amino acid residue or residues not included in the above two amino acid sequences. A beta-alanine or aminohexanoyl spacer may also be used as the linker.

In another embodiment, the amino acid sequence (1) and amino acid sequence (2) are linked directly. In this case, no amino acid sequence that does not form part of these amino acid sequences is present between the amino acid sequence (1) and the amino acid sequence (2).

The antiviral peptide may also include a sequence (amino acid residues) other than the amino acid sequences constituting the amino acid sequence (1) and the amino acid sequence (2) as long as the antiviral activity of suppressing the proliferation of at least one kind of virus is not compromised.

In the antiviral peptide disclosed here, the total number of amino acid residues constituting the peptide chain is appropriately not more than 100. From the standpoint of manufacturing costs and ease of synthesis and handling, the total number of amino acid residues is preferably not more than 80, or more preferably not more than 70, or still more preferably not more than 60. The total number of amino acid residues may also be not more than 50. A peptide with such a relatively short chain length is easy to chemically synthesize, allowing the antiviral peptide to be provided easily. Although not particularly limited, a straight chain or helix shape is preferred for avoiding immunogenicity (antigenicity). A peptide with such a shape is unlikely to form an epitope.

The ratio of the combined amino acid residues of the amino acid sequence (1) and the amino acid sequence (2) as a percentage of the total amino acid residues constituting the synthesized peptide is not particularly limited as long as antiviral activity is retained, but this ratio is generally at least 80%, or at least 85%, or preferably at least 90%. Preferably all the amino acid residues are L-amino acids, but D-amino acids may be substituted for some or all of the amino acid residues as long as antiviral activity is retained.

Preferably at least one amino acid residue has been amidated in the antiviral peptide disclosed here. The structural stability (such as protease resistance) of the synthetic peptide can be improved by amidating a carboxyl group of an amino acid residue (typically the C-terminal amino acid residue of the peptide chain).

In a certain embodiment, the amino acid sequence (1) constitutes the C-terminal part of the antiviral peptide disclosed here. In this case, the C-terminal amino acid residue of the amino acid sequence (1) is amidated. In a preferred embodiment, the amino acid sequence (2) constituters the C-terminal part of the antiviral peptide. In this case, the C-terminal amino acid residue of the amino acid sequence (2) is amidated as a way of stabilizing the antiviral peptide.

The antiviral peptide disclosed here can be easily manufactured by ordinary chemical synthesis methods. For example, either a conventional known solid-phase synthesis method or liquid-phase synthesis method may be used. Solid-phase synthesis using Boc (t-butyloxycarbonyl) or Fmoc (9-fluorenylmethoxycarbonyl) as an amino protecting group is desirable.

For the antiviral peptide disclosed here, a peptide chain having the desired amino acid sequence and modifications (C-terminal amidation, etc.) can be synthesized by solid-phase synthesis using a commercial peptide synthesizer.

The antiviral peptide may also be biosynthesized based on genetic engineering methods. That is, a polynucleotide (typically DNA) is synthesized with a nucleotide sequence (including the ATG initiation codon) coding for the amino acid sequence of the desired antiviral peptide. A recombinant vector having a gene expression construct including the synthesized polynucleotide (DNA) together with various regulatory elements for expressing this amino acid sequence in a host cell (including a promoter, a ribosome binding site, a terminator, an enhancer, and various cis-elements for regulating expression level) is then constructed according to the host cell.

This recombinant vector is introduced into a predetermined host cell (such as a yeast, insect or plant cell) by ordinary methods, and the host cell or a tissue or organism containing the host cell is cultured under predetermined conditions. It is thus possible to express and product the target peptide in cells. The peptide can then be isolated from the host cells (or from medium if it has been secreted), and refolded, purified or the like as necessary to obtain the target antiviral peptide.

Conventional methods in the field may be adopted as the methods for constructing the recombinant vector and introducing the recombinant vector into the host cell, and detailed explanations are omitted because these methods themselves are not a particular feature of the invention.

Alternatively, template DNA for a cell-free protein synthesis system (that is, a synthetic gene fragment containing a nucleotide sequence coding for the amino acid sequence of the antiviral peptide) may be constructed, and the target polypeptide can then by synthesized in vitro with a cell-free protein synthesis system using the template DNA together with various compounds necessary for peptide synthesis (ATP, RNA polymerase, amino acids, etc.). The literature of Shimizu et al. (Shimizu et al., Nature Biotechnology 19, 751-755 (2001)) and Madin et al. (Madin et al., Proc. Natl. Acad. Sci USA, 97(2), 559-564 (2000)) may be consulted with respect to cell-free protein synthesis systems. Based on the technology described in this literature, many firms are already engaged in contract production of peptides at the time of this application, and cell-free protein synthesis kits are commercially available (from CellFree Sciences in Japan for example).

A single- or double-stranded polynucleotide containing a nucleotide sequence coding for the antiviral peptide disclosed here or a nucleotide sequence complementary to that nucleotide sequence can be easily manufactured (synthesized) by conventional known methods. That is, a nucleotide sequence corresponding to the amino acid sequence of the antiviral peptide can be easily determined and provided by selecting codons corresponding to each of the amino acid residues constituting the designed amino acid sequence. Once the nucleotide sequence has been determined, a (single-stranded) polynucleotide corresponding to the desired nucleotide sequence can be easily obtained using a DNA synthesizer or the like. The resulting single-stranded DNA can then be used as a template to obtain the target double-stranded DNA by various enzymatic synthesis methods (typically PCR). The polynucleotide may be in the form of either DNA or RNA (mRNA or the like). Either double-stranded or single-stranded DNA may be provided. When the DNA is single-stranded, it may be either a coding strand (sense strand) or a non-coding strand (antisense strand) complementary to the coding strand.

As discussed above, the resulting polynucleotide can be used as a material for constructing a recombinant gene (expression cassette) for producing the antiviral peptide in various host cells or with a cell-free protein synthesis system.

A polynucleotide coding for the antiviral peptide may also be used as a material for so-called gene therapy. For example, a gene coding for the antiviral peptide (typically a DNA segment or RNA segment) may be incorporated into a suitable vector and introduced into a target site to thereby cause constant expression of the antiviral peptide of the invention in a living body (cells). Consequently, a polynucleotide (DNA segment, RNA segment or the like) coding for the antiviral peptide of the invention can be used as a drug for preventing or treating viral infection.

The antiviral peptide disclosed here may be used suitably as an active component of a composition for suppressing (or inhibiting) the proliferation of at least one kind of virus (that is, as a pharmacological antiviral composition such as an antiviral agent).

The antiviral peptide contained in the antiviral composition (antiviral agent) may also be in the form of a salt as long as antiviral activity is retained. For example, it is possible to use an acid-addition salt of the peptide obtained by adding and reacting an inorganic acid or organic acid commonly used in ordinary methods. Another salt (such as a metal) salt is also possible as long as antiviral activity is retained. The "peptide" described in this Description and the Claims encompasses such salt forms.

The antiviral composition disclosed here may contain various pharmacologically (pharmaceutically) acceptable carriers suited to the dosage form as long as the antiviral activity of the antiviral peptide as an active ingredient is not lost. For example, carriers commonly used as diluents, excipients and the like in peptide drugs may be used.

These may differ depending on the use and form of the antiviral composition disclosed here, but typically include water, physiological buffers and various organic solvents. Aqueous solutions of alcohols (such as ethanol) in suitable concentrations are also possible, as are glycerol and non-drying oils such as olive oil, as well as liposomes. Other examples of secondary components that may be included in the antiviral composition include various fillers, bulking agents, binders, humectants, surfactants, dyes, perfumes and the like.

Typical forms of the antiviral composition (antiviral agent) include liquids, suspensions, emulsions, aerosols, foams, granules, powders, tablets, capsules, ointments, aqueous gels and the like. For injection purposes, the composition may also be in the form of a freeze-dried product or granules that are dissolved in physiological saline or a suitable buffer (such as PBS) or the like immediately before use to prepare a drug solution.

The processes for preparing compositions (agents) of various forms from the antiviral peptide (principal component) and various carriers (secondary components) may conform to conventional known methods, and detailed explanations of these methods are omitted because they are not a feature of the invention. Sources of detailed information about formulations include Comprehensive Medicinal Chemistry, Corwin Hansch Ed., Pergamon Press (1990), the entire contents whereof are herein incorporated by reference.

The virus targeted for proliferation suppression by the antiviral composition (antiviral peptide) disclosed here may be any virus without limitations, including a variety of viruses that infect humans and non-human mammals. As described in the examples below, the antiviral composition (antiviral peptide) disclosed here has a wide antiviral spectrum and can suppress the proliferation of a variety of viruses. The virus targeted for proliferation suppression includes various DNA viruses having DNA viral genomes, and various RNA viruses having RNA viral genomes. Desirable examples of the virus targeted for proliferation suppression that are RNA viruses include viruses in the Rhabdoviridae family (such as Vesicular stomatitis virus (VSV)) and viruses having glycoproteins of Filoviruses (such as Ebola virus and Marburg virus). Viruses having glycoproteins of Filoviruses include Filoviruses themselves and recombinant viruses expressing Filovirus glycoproteins.

The antiviral composition (antiviral peptide) disclosed here may be used for treating and preventing viral infections, such as by oral cleansing (gargling), washing of extracted tissue, and washing of instruments and the like.

The antiviral composition (antiviral peptide) disclosed here may be used in methods and dosages according to its form and purpose.

The antiviral peptide disclosed here can maintain antiviral activity even in systems containing relatively high concentrations of cations, salts (such as sodium chloride) or organic matter such as serum. Thus, the antiviral composition disclosed here is suited for use in systems (places) wherein cations, salts, serum and the like are present. For example, the antiviral composition provided by the present invention in a liquid form can be administered to a patient either as an intravenous, intramuscular, subcutaneous, intradermal or intraperitoneal injection, or as an enema.

A solid form such as a tablet may also be administered orally. When used for washing sanitary ceramic surfaces, moreover, a liquid containing a relatively high concentration (such as 1 mg/ml to 100 mg/ml) of the antiviral peptide may be sprayed directly on a target surface or applied to a cloth or paper and used to wipe a target surface. These are only examples, and the composition may be used in the same forms and by the same methods as conventional peptide antibiotics, agricultural chemicals, and quasi-drugs containing peptides.

A suitable quantity of the antiviral composition disclosed here (that is, a suitable quantity of the synthetic peptide) may also be provided at least once to a medium containing target cultured cells (tissue or the like) that are being cultured in vitro (including cultured cell lines as well as cell masses, tissue and organs extracted from living bodies). The supplied amount per application and the number of applications are not particularly limited and may differ depending on the conditions including the type of cells being cultured, the cell density (cell density at beginning of culture), number of passages, culture conditions, type of medium and the like, but preferably the synthetic peptide is added once, twice or more times so that the concentration of the synthetic peptide in the medium is in the range of about from 0.5 µM to 100 µM, or preferably from 3 µM to 50 µM (such as from 5 µM to 30 µM).

Recently in the field of genetic engineering, recombinant VSV has sometimes been used as a virus vector for introducing target genes into cells, tissues or organs. Pseudotype viruses are also sometimes prepared for purposes of analyzing the functions of virus proteins of other viruses (such as Filoviruses and Retroviruses). For example, a Filovirus glycoprotein may be incorporated into VSV be genetic manipulation to prepare a VSV expressing the Filovirus glycoprotein. Conventionally, such VSVs are used to analyze the functions of Filovirus glycoproteins, or to develop preventative and therapeutic drugs for Filoviruses. For example, as shown in the examples below, undesirable viral infections of organs, tissues, cells and the like in culture can be prevented and viral proliferation in hosts can be suppressed by including the antiviral peptide disclosed here in culture liquid at a suitable concentration.

Detailed information about pathogenic viruses is required for developing preventative agents and antiviral drugs. For example, according to the examples below the antiviral peptide disclosed here may be applied as a research tool to the analysis of various viral infections and proliferation mechanisms.

Treatment and prevention of livestock diseases (with vaccines and antiviral drugs for example) is essential for environment management and quality control in livestock breeding, and accurate information about the pathogens that cause disease is also necessary. Because the antiviral peptide disclosed here can itself be a promising seed material for anti-VSV agents, it holds promise for the prevention of viral infection in livestock, preventing the spread of infection among livestock, and establishing preventative and treatment methods for those such as livestock workers and veterinarians who may have close contact with domestic animals.

Since the antiviral peptide disclosed here has been confirmed to have proliferation suppression effects with respect to recombinant viruses expressing Filovirus glycoproteins as described in the examples below, it is expected to have proliferation suppression effects against Filoviruses. Consequently, this antiviral peptide can be a seed material for anti-Filovirus agent and holds great promise for the establishment of methods for treating Filovirus infection (Ebola hemorrhagic fever, Marburg hemorrhagic fever).

Some examples of the present invention are explained below, but not with the intent of limiting the invention to what is shown in the examples.

Example 1

<Peptide Synthesis>

The 10 peptides shown in Table 1 were manufactured with a peptide synthesizer, specifically as follows.

Sample 1 is a synthetic peptide represented by SEQ ID NO:29, using the amino acid sequence represented by SEQ ID NO:4 as the amino acid sequence (1), and containing the amino acid sequence represented by SEQ ID NO:24 (NoLS of LIM kinase 2) as the amino acid sequence (2) at the C-terminal end. The amino acid sequence (2) is joined to the C-terminal of the amino acid sequence (1) via a linker consisting of 3 amino acid residues.

Sample 2 is a synthetic peptide represented by SEQ ID NO:30, using the amino acid sequence represented by SEQ ID NO:6 as the amino acid sequence (1), and containing the amino acid sequence represented by SEQ ID NO:24 (NoLS of LIM kinase 2) as the amino acid sequence (2) at the C-terminal end. The amino acid sequence (2) is joined to the C-terminal of the amino acid sequence (1) via a linker consisting of 3 amino acid residues.

Sample 3 is a synthetic peptide represented by SEQ ID NO:31, containing the amino acid sequence represented by SEQ ID NO:5 as the amino acid sequence (1) and the amino acid sequence represented by SEQ ID NO:24 (NoLS of LIM kinase 2) as the CPP sequence (2). The amino acid sequence (2) is joined to the C-terminal of the amino acid sequence (1) via a linker consisting of 3 amino acid residues.

Sample 4 is a synthetic peptide represented by SEQ ID NO:32, using the amino acid sequence represented by SEQ ID NO:7 as the amino acid sequence (1), and containing the amino acid sequence represented by SEQ ID NO:24 (NoLS of LIM kinase 2) as the amino acid sequence (2) at the C-terminal end. The amino acid sequence (2) is joined to the C-terminal of the amino acid sequence (1) via a linker consisting of 3 amino acid residues.

Sample 5 is a synthetic peptide represented by SEQ ID NO:33, using the amino acid sequence represented by SEQ ID NO:8 as the amino acid sequence (1), and containing the amino acid sequence represented by SEQ ID NO:24 (NoLS of LIM kinase 2) as the amino acid sequence (2) at the C-terminal end. The amino acid sequence (2) is joined to the C-terminal of the amino acid sequence (1) via a linker consisting of 3 amino acid residues.

Sample 6 is a synthetic peptide represented by SEQ ID NO:34, using the amino acid sequence represented by SEQ ID NO:10 as the amino acid sequence (1), and containing the amino acid sequence represented by SEQ ID NO:24 (NoLS of LIM kinase 2) as the amino acid sequence (2) at the C-terminal end. The amino acid sequence (2) is joined to the C-terminal of the amino acid sequence (1) via a linker consisting of 3 amino acid residues.

Sample 7 is a synthetic peptide represented by SEQ ID NO:35, using the amino acid sequence represented by SEQ ID NO:9 as the amino acid sequence (1), and containing the amino acid sequence represented by SEQ ID NO:24 (NoLS of LIM kinase 2) as the amino acid sequence (2) at the C-terminal end. The amino acid sequence (2) is joined to the C-terminal of the amino acid sequence (1) via a linker consisting of 3 amino acid residues.

Sample 8 is a synthetic peptide represented by SEQ ID NO:36, using the amino acid sequence represented by SEQ ID NO:39 as the amino acid sequence (1), and containing the amino acid sequence represented by SEQ ID NO:24 (NoLS of LIM kinase 2) as the amino acid sequence (2) at the C-terminal end. SEQ ID NO:39 represents a TM sequence consisting of a total of 19 amino acid residues contained in a glycoprotein of one kind of isolated VSV (Vesicular stomatitis Piry virus) (UniProtKB-Q85213).

Sample 9 is a synthetic peptide represented by SEQ ID NO:37, using the amino acid sequence represented by SEQ ID NO:40 as the amino acid sequence (1), and containing the amino acid sequence represented by SEQ ID NO:24 (NoLS of LIM kinase 2) as the amino acid sequence (2) at the C-terminal end. SEQ ID NO:40 represents a TM sequence consisting of a total of 21 amino acid residues contained in a glycoprotein of a kind of isolated VSV (Vesicular stomatitis Indiana virus) (UniProtKB-P05322).

Sample 10 is a synthetic peptide represented by SEQ ID NO:38, using the amino acid sequence represented by SEQ ID NO:41 as the amino acid sequence (1), and containing the amino acid sequence represented by SEQ ID NO:24 (NoLS of LIM kinase 2) as the amino acid sequence (2) at the C-terminal end. SEQ ID NO:41 represents a TM sequence consisting of a total of 21 amino acid residues contained in a glycoprotein of a kind of isolated VSV (Vesicular stomatitis New Jersey virus) (UniProtKB-P04882).

TABLE 1

| Sample Name | Amino acid sequence | The number of Amino acid residues | SEQ ID NO |
| --- | --- | --- | --- |
| 1 | SDWGVLTNLG ILLLLSIAVL IALSCICGSG KKRTLRKNDR KKR | 43 | 29 |
| 2 | RQWIPAGIGV TGVIIAVIAL | 43 | 30 |

TABLE 1-continued

| Sample Name | Amino acid sequence | The number of Amino acid residues | SEQ ID NO |
|---|---|---|---|
| | FCICKFVGSG KKRTLRKNDR KKR | | |
| 3 | RQWIPAGIGI TGIIIAIIAL LCVCKLLGSG KKRTLRKNDR KKR | 43 | 31 |
| 4 | MGVTGILQLP RDRFKRTSFF LWVIILFQRT FSGSGKKRTL RKNDRKKR | 48 | 32 |
| 5 | MEGLSLLQLP RDKFRKSSFF VWVIILFQKA FSGSGKKRTL RKNDRKKR | 48 | 33 |
| 6 | MKTTCFLISL ILQGTKNGSG KKRTLRKNDR KKR | 34 | 34 |
| 7 | MKTTCLLISL IQGCKTGSGK KRTLRKNDRK KR | 34 | 35 |
| 8 | NAIVGIVLLI VVTFLAIKTK KRTLRKNDRK KR | 32 | 36 |
| 9 | FFFIIGLIIG LFLVLRVGIH LKKRTLRKND RKKR | 34 | 37 |
| 10 | VLAVIIGFVI LMFLIKLIGV LKKRTLRKND RKKR | 34 | 38 |

The peptides of samples 1 to 10 were all synthesized by performing solid-phase synthesis (Fmoc method) using a commercial peptide synthesizer in accordance with the manual. The mode of use of the peptide synthesizer is not explained in detail because it is not a feature of the invention. In all of the synthetic peptides provided for testing, the carboxyl group (—COOH) of the C-terminal amino acid has been amidated (—CONH$_2$).

The peptides of each synthesized sample were dissolved in DMSO to prepare stock solutions of each sample peptide (concentration 2.5 mM).

<Cells and Virus>

The details of the cells and viruses used in the following evaluation tests are as follows.

The cells used in the following evaluation tests were African green monkey kidney epithelium Vero E6 cells. The Vero E6 cells were cultured using Dulbecco's Modified Eagle Medium (DMEM) containing L-glutamine, 100 U/ml of penicillin, 0.1 mg/ml of streptomycin and 10% FCS.

Human fetal kidney-derived 293T cells were also used to obtain viruses for use in the following evaluation tests. The 293T cells were cultured using Dulbecco's Modified Eagle Medium (DMEM) containing L-glutamine, 100 U/ml of penicillin, 0.1 mg/ml of streptomycin and 10% FCS.

The viruses targeted for proliferation suppression in the evaluation tests are three viruses, a virus having an Ebola virus (Zaire) glycoprotein substituted for a VSV glycoprotein (VSV-ZGP), a virus having an Ebola virus (Sudan) glycoprotein substituted for a VSV glycoprotein (VSV-SGP) and a virus having a Marburg virus (Angola) glycoprotein substituted for a VSV glycoprotein (VSV-AGP).

These three viruses were prepared based on the methods described in the papers of Takada et al (Takada et al., Proc. Natl. Acad. Sci. 94, 14764-14769, 1997 and Takada et al., J. Virol. 77, 1069-1074, 2003) and Nakayama et al (Nakayama et al., J. Infect. Dis. 204 Suppl. 3, S978-S985, 2011).

Briefly, recombinant VSVs were prepared including the full-length VSV genome in which the nucleotide sequence of the VSV G protein gene had been substituted with the region coding for Ebola virus (Zaire and Sudan) or Marburg virus (Angola) glycoproteins. The infected culture supernatant was collected and centrifuged, and the centrifugal supernatant was obtained as VSV-ZGP, VSV-SGP and VSV-AGP virus stocks.

The titers (infection titers) of the three viruses were all measured based on commonly known plaque assay methods.

The data about the nucleotide sequences of the cDNA coding for the Ebola virus (Zaire) glycoprotein, the cDNA coding for the Ebola virus (Sudan) glycoprotein and the cDNA coding for the Marburg virus (Angola) glycoprotein used to obtain the three Filovirus glycoprotein-expressing plasmids was obtained using known databases (UniProt, GenBank, etc.). The nucleotide sequence data here was obtained based on data obtained from the UniProt access numbers Q05320, Q66798 and Q1PD50.

<Antiviral Evaluation Test>

The details of the evaluation test are as follows.

The three previously prepared viruses VSV-ZGP, VSV-SGP and VSV-AGP were each diluted to prepare virus suspensions with infection titers of $10^3$ PFU/ml. 2% FCS-containing DMEM was used as the virus diluent.

Vero E6 cells that had been cultured in advance on commercial 6-well plates were washed with 1 ml of PBS per well. 1 ml of the above virus suspension was then added to each well to inoculate the Vero E6 cells with the virus. The 6-well plates were incubated at 37° C. for about 1 hour, the viral suspension was removed from the wells, and the cells were washed once each with PBS and DMEM.

Culture solutions containing the above sample peptides 1 to 6 and 8 to 10 were then supplied to the 6-well plates in the amount of 2 ml per well, and the cells were cultured at 37° C. The concentration of the sample peptides 1 to 6 was 20 μM, and the concentration of the sample peptides 8 to 10 was 50 μM. Culture solution to which DMSO had been added in the same amount as the sample peptide-containing culture solution was also used as a control. 2% FCS in DMEM was used for the culture solution.

The culture supernatant was collected 1, 2 and 3 days after the start of culture. Using Vero E6 cells that had not been infected with any virus, the virus infection titer contained in the culture supernatant was calculated by a known ordinary TCID$_{50}$ method. The calculated virus infection titer (TCID$_{50}$/ml) is given here as the amount of the virus contained in the culture supernatant.

Figure 2:
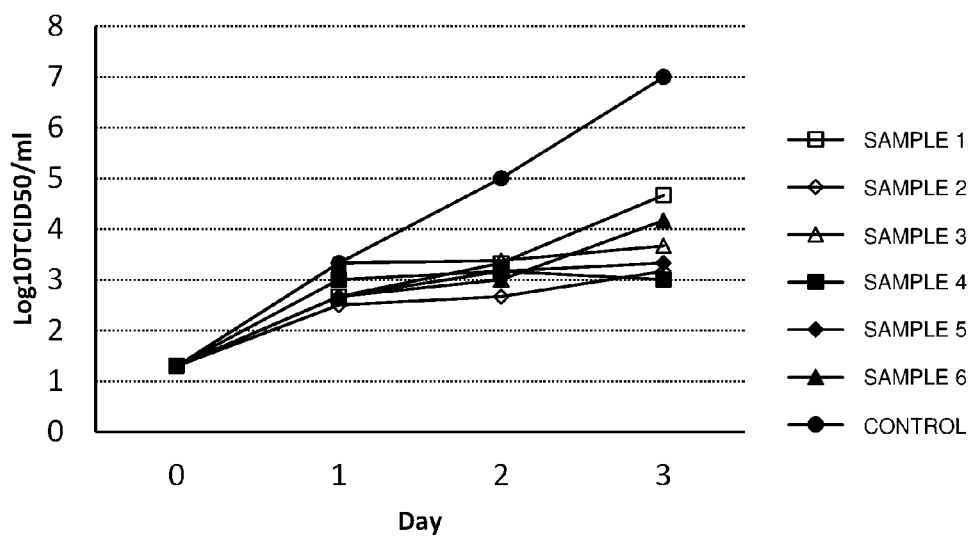
FIG. 2 is a graph showing changes over time in Example 1 in the viral load ($Log_{10}$ $TCID_{50}$/ml) in culture supernatant of Vero E6 cells that were cultured for 1, 2 and 3 days after inoculation with $10^3$ PFU of VSV-SGP and subsequent addition of any of the sample peptides 1 to 6 to a concentration of 20 μM, or with no sample peptide added.
Figure 3:
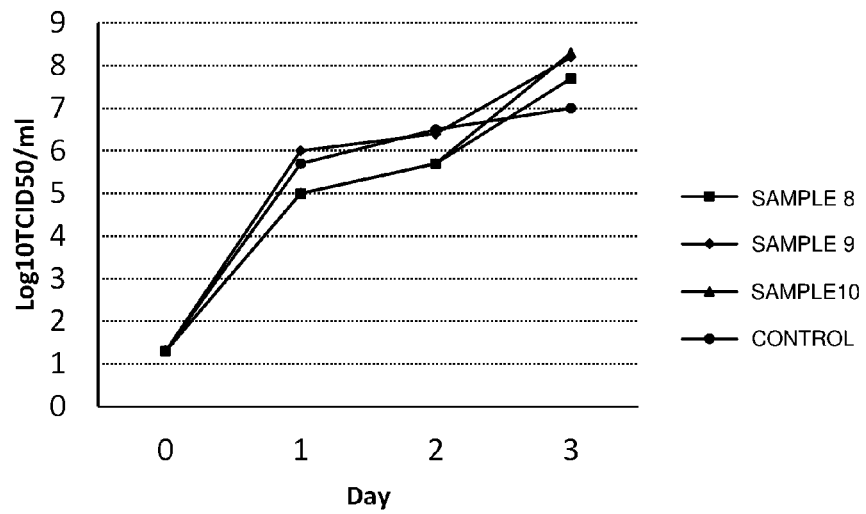
FIG. 3 is a graph showing changes over time in Example 1 in the viral load ($Log_{10}$ $TCID_{50}$/ml) in culture supernatant of Vero E6 cells that were cultured for 1, 2 and 3 days after inoculation with $10^3$ PFU of VSV-ZGP and subsequent addition of any of the sample peptides 8 to 10 to a concentration of 50 μM, or with no sample peptide added.

The results are shown in FIGS. 1 to 3.

Example 2

In Example 2, an antiviral evaluation test was performed using a total of 9 sample peptides used in Example 1.

In this antiviral evaluation test, the virus targeted for proliferation suppression was VSV. VSV was diluted to prepare a virus suspension with an infection titer of $10^3$ PFU/ml. Using this virus suspension, Vero E6 cells were inoculated with VSV. Apart from this, the antiviral evaluation test of Example 2 was performed with the same materials and by the same methods as in Example 1.

Figure 4:
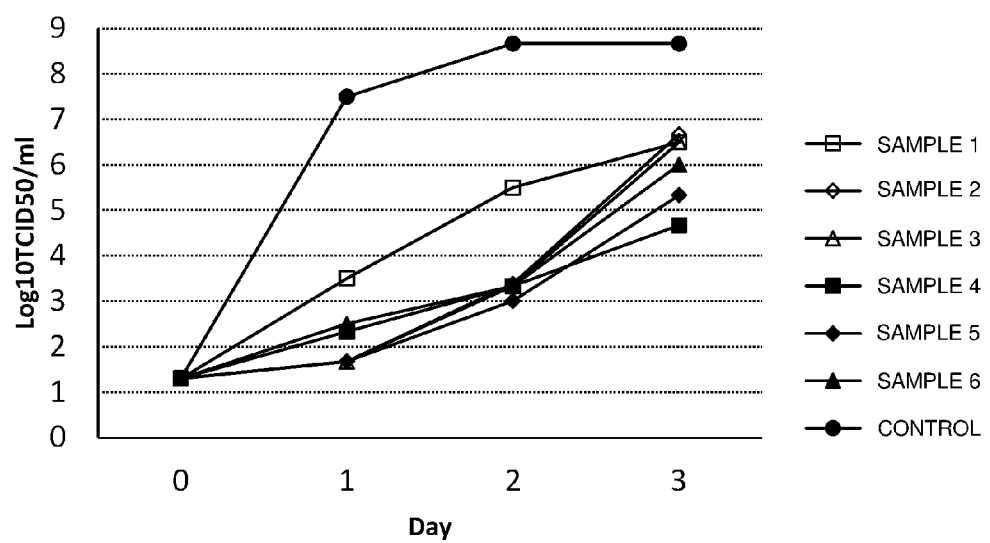
FIG. 4 is a graph showing changes over time in Example 2 in the viral load ($Log_{10}$ $TCID_{50}$/ml) in culture supernatant of Vero E6 cells that were cultured for 1, 2 and 3 days after inoculation with $10^3$ PFU of VSV and subsequent addition of any of the sample peptides 1 to 6 to a concentration of 20 μM, or with no sample peptide added.
Figure 5:
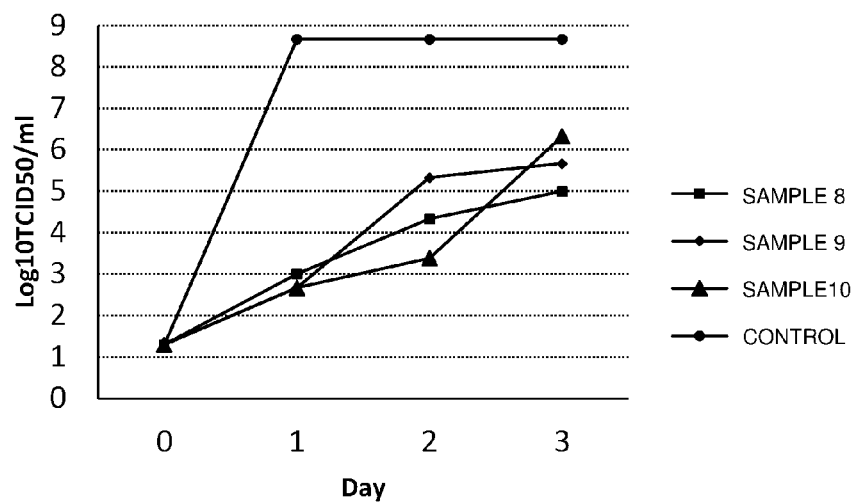
FIG. 5 is a graph showing changes over time in Example 2 in the viral load ($Log_{10}$ $TCID_{50}$/ml) in culture supernatant of Vero E6 cells that were cultured for 1, 2 and 3 days after inoculation with $10^3$ PFU of VSV and subsequent addition of any of the sample peptides 8 to 10 to a concentration of 50 μM, or with no sample peptide added.

The results are shown in FIGS. 4 and 5.

[Results and Discussion]

In Example 1, as shown in FIGS. 1 and 2, with samples 1 to 6 the amount of the virus contained in the culture supernatant of the Vero E6 cells inoculated with VSV-ZGP and the Vero E6 cells inoculated with VSV-SGP was less than the amount of the virus contained in the control culture supernatant 2 and 3 days after the sample peptide was supplied. Although the exact data are not shown, the amount of the virus contained in the culture supernatant of Vero E6 cells inoculated with VSV-AGP was also less than the amount of the virus contained in the control culture supernatant 2 and 3 days after the sample peptide was supplied. In Example 2, as shown in FIG. 4, the amount of the virus contained in the culture supernatant of the Vero E6 cells inoculated with VSV was also less than the amount of the virus contained in the control culture supernatant 1 day after the sample peptide was supplied. This confirms that the sample peptides 1 to 6 all exhibit a proliferation suppression effect against the four kinds of viruses described above.

With the sample peptides 8 to 10, on the other hand, a proliferation suppression effect was confirmed against VSV (FIG. 5) but not against VSV-ZGP (FIG. 3). This shows that the sample peptides 1 to 6 exhibit proliferation suppression effects against more viruses than do the sample peptides 8 to 10.

The results of Examples 1 and 2 above confirmed that the synthetic peptide disclosed here suppresses the proliferation of at least one kind of virus due to having an amino acid sequence (1) and an amino acid sequence (2) (that is, a CPP sequence).

Specific examples of the present invention were explained above, but these are only examples and do not limit the scope of the Claims. The technology described in the Claims encompasses various changes and modifications to the specific examples given above.

For example, a modified sequence of an amino acid sequence of SEQ ID NOS:1 to 10 may be used as the amino acid sequence (1). Similarly, a polyarginine or a known CPP sequence other than the CPP sequences used in the above examples (such as the CPP sequences represented by SEQ ID NOS:11 to 23 and 25 to 28) may be used as the amino acid sequence (2).

As discussed above, viral proliferation can be suppressed (the spread of viral infection can be prevented) with the antiviral peptide disclosed here. Consequently, an antiviral composition (antiviral agent) having a proliferation suppression effect against at least one kind of virus can be provided by using the antiviral peptide provided by the present invention.

---

The invention claimed is:

1. A synthetic peptide that suppresses proliferation of at least one kind of virus, comprising the amino acid sequence represented by any of SEQ ID NOs:29 to 35, wherein the total number of amino acid residues in the synthetic peptide is not more than 100.

2. An antiviral composition for suppressing proliferation of at least one kind of virus, comprising, a synthetic peptide comprising the amino acid sequence represented by any of SEQ ID NOs:29 to 35, and at least one kind of pharmacologically acceptable carrier, wherein the total number of amino acid residues in the synthetic peptide is not more than 100.

* * * * *

SEQUENCE LISTING

```
<160> NUMBER OF SEQ ID NOS: 41

<210> SEQ ID NO 1
<211> LENGTH: 21
<212> TYPE: PRT
<213> ORGANISM: Lake Victoria marburgvirus

<400> SEQUENCE: 1

Trp Gly Val Leu Thr Asn Leu Gly Ile Leu Leu Leu Leu Ser Ile Ala
1               5                   10                  15

Val Leu Ile Ala Leu
            20

<210> SEQ ID NO 2
<211> LENGTH: 21
<212> TYPE: PRT
<213> ORGANISM: Sudan ebolavirus

<400> SEQUENCE: 2

Trp Ile Pro Ala Gly Ile Gly Ile Thr Gly Ile Ile Ile Ala Ile Ile
1               5                   10                  15

Ala Leu Leu Cys Val
            20

<210> SEQ ID NO 3
<211> LENGTH: 21
<212> TYPE: PRT
<213> ORGANISM: Zaire ebolavirus

<400> SEQUENCE: 3

Trp Ile Pro Ala Gly Ile Gly Val Thr Gly Val Ile Ile Ala Val Ile
1               5                   10                  15
```

Ala Leu Phe Cys Ile
            20

<210> SEQ ID NO 4
<211> LENGTH: 27
<212> TYPE: PRT
<213> ORGANISM: Lake Victoria marburgvirus

<400> SEQUENCE: 4

Ser Asp Trp Gly Val Leu Thr Asn Leu Gly Ile Leu Leu Leu Leu Ser
1               5                   10                  15

Ile Ala Val Leu Ile Ala Leu Ser Cys Ile Cys
            20                  25

<210> SEQ ID NO 5
<211> LENGTH: 27
<212> TYPE: PRT
<213> ORGANISM: Sudan ebolavirus

<400> SEQUENCE: 5

Arg Gln Trp Ile Pro Ala Gly Ile Gly Ile Thr Gly Ile Ile Ile Ala
1               5                   10                  15

Ile Ile Ala Leu Leu Cys Val Cys Lys Leu Leu
            20                  25

<210> SEQ ID NO 6
<211> LENGTH: 27
<212> TYPE: PRT
<213> ORGANISM: Zaire ebolavirus

<400> SEQUENCE: 6

Arg Gln Trp Ile Pro Ala Gly Ile Gly Val Thr Gly Val Ile Ile Ala
1               5                   10                  15

Val Ile Ala Leu Phe Cys Ile Cys Lys Phe Val
            20                  25

<210> SEQ ID NO 7
<211> LENGTH: 32
<212> TYPE: PRT
<213> ORGANISM: Zaire ebolavirus

<400> SEQUENCE: 7

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

<210> SEQ ID NO 8
<211> LENGTH: 32
<212> TYPE: PRT
<213> ORGANISM: Sudan ebolavirus

<400> SEQUENCE: 8

Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

<210> SEQ ID NO 9
<211> LENGTH: 18
<212> TYPE: PRT
<213> ORGANISM: Lake Victoria marburgvirus -continued

```
<400> SEQUENCE: 9

Met Lys Thr Thr Cys Leu Leu Ile Ser Leu Ile Leu Ile Gln Gly Val
1               5                   10                  15

Lys Thr

<210> SEQ ID NO 10
<211> LENGTH: 18
<212> TYPE: PRT
<213> ORGANISM: Marburg marburgvirus

<400> SEQUENCE: 10

Met Lys Thr Thr Cys Phe Leu Ile Ser Leu Ile Leu Ile Gln Gly Thr
1               5                   10                  15

Lys Asn

<210> SEQ ID NO 11
<211> LENGTH: 14
<212> TYPE: PRT
<213> ORGANISM: Artificial Sequence
<220> FEATURE:
<223> OTHER INFORMATION: synthetic peptide

<400> SEQUENCE: 11

Arg Ser Arg Lys Tyr Thr Ser Trp Tyr Val Ala Leu Lys Arg
1               5                   10

<210> SEQ ID NO 12
<211> LENGTH: 19
<212> TYPE: PRT
<213> ORGANISM: Artificial Sequence
<220> FEATURE:
<223> OTHER INFORMATION: synthetic peptide

<400> SEQUENCE: 12

Met Ala Lys Ser Ile Arg Ser Lys His Arg Arg Gln Met Arg Met
1               5                   10                  15

Lys Arg Glu

<210> SEQ ID NO 13
<211> LENGTH: 16
<212> TYPE: PRT
<213> ORGANISM: Artificial Sequence
<220> FEATURE:
<223> OTHER INFORMATION: synthetic peptide

<400> SEQUENCE: 13

Met Ala Arg Arg Arg Arg His Arg Gly Pro Arg Arg Pro Arg Pro Pro
1               5                   10                  15

<210> SEQ ID NO 14
<211> LENGTH: 19
<212> TYPE: PRT
<213> ORGANISM: Artificial Sequence
<220> FEATURE:
<223> OTHER INFORMATION: synthetic peptide

<400> SEQUENCE: 14

Gly Arg Cys Arg Arg Leu Ala Asn Phe Gly Pro Arg Lys Arg Arg Arg
1               5                   10                  15

Arg Arg Arg

<210> SEQ ID NO 15
```

-continued

```
<211> LENGTH: 16
<212> TYPE: PRT
<213> ORGANISM: Artificial Sequence
<220> FEATURE:
<223> OTHER INFORMATION: synthetic peptide

<400> SEQUENCE: 15

Arg Arg Arg Lys Arg Asn Arg Asp Ala Arg Arg Arg Arg Lys Gln
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: synthetic peptide

<400> SEQUENCE: 16

Met Gln Arg Lys Pro Thr Ile Arg Arg Lys Asn Leu Arg Leu Arg Arg
1               5                   10                  15

Lys

<210> SEQ ID NO 17
<211> LENGTH: 7
<212> TYPE: PRT
<213> ORGANISM: Artificial Sequence
<220> FEATURE:
<223> OTHER INFORMATION: synthetic peptide

<400> SEQUENCE: 17

Ile Met Arg Arg Arg Gly Leu
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic peptide

<400> SEQUENCE: 18

Lys Lys Leu Lys Lys Arg Asn Lys
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic peptide

<400> SEQUENCE: 19

Arg Arg Arg Ala Asn Asn Arg Arg Arg
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Arg Lys Lys Arg Lys Lys Lys
1               5
```

```
<210> SEQ ID NO 21
<211> LENGTH: 15
<212> TYPE: PRT
<213> ORGANISM: Artificial Sequence
<220> FEATURE:
<223> OTHER INFORMATION: synthetic peptide

<400> SEQUENCE: 21

Lys Arg Lys Gly Lys Leu Lys Asn Lys Gly Ser Lys Arg Lys Lys
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: synthetic peptide

<400> SEQUENCE: 22

Ser Lys Arg Leu Ser Ser Arg Ala Arg Lys Arg Ala Ala Lys Arg Arg
1               5                   10                  15

Leu Gly

<210> SEQ ID NO 23
<211> LENGTH: 14
<212> TYPE: PRT
<213> ORGANISM: Artificial Sequence
<220> FEATURE:
<223> OTHER INFORMATION: synthetic peptide

<400> SEQUENCE: 23

Lys Arg Pro Arg Arg Arg Pro Ser Arg Pro Phe Arg Lys Pro
1               5                   10

<210> SEQ ID NO 24
<211> LENGTH: 13
<212> TYPE: PRT
<213> ORGANISM: Artificial Sequence
<220> FEATURE:
<223> OTHER INFORMATION: synthetic peptide

<400> SEQUENCE: 24

Lys Lys Arg Thr Leu Arg Lys Asn Asp Arg Lys Lys Arg
1               5                   10

<210> SEQ ID NO 25
<211> LENGTH: 8
<212> TYPE: PRT
<213> ORGANISM: Artificial Sequence
<220> FEATURE:
<223> OTHER INFORMATION: synthetic peptide

<400> SEQUENCE: 25

Trp Arg Arg Gln Ala Arg Phe Lys
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic peptide

<400> SEQUENCE: 26

Arg Lys Lys Arg Arg Gln Arg Arg Arg
1               5
```

<210> SEQ ID NO 27
<211> LENGTH: 11
<212> TYPE: PRT
<213> ORGANISM: Artificial Sequence
<220> FEATURE:
<223> OTHER INFORMATION: synthetic peptide

<400> SEQUENCE: 27

Tyr Ala Arg Ala Ala Ala Arg Gln Ala Arg Ala
1               5                   10

<210> SEQ ID NO 28
<211> LENGTH: 18
<212> TYPE: PRT
<213> ORGANISM: Artificial Sequence
<220> FEATURE:
<223> OTHER INFORMATION: synthetic peptide

<400> SEQUENCE: 28

Lys Gly Arg Gln Val Lys Val Trp Phe Gln Asn Arg Arg Met Lys Trp
1               5                   10                  15

Lys Lys

<210> SEQ ID NO 29
<211> LENGTH: 43
<212> TYPE: PRT
<213> ORGANISM: Artificial Sequence
<220> FEATURE:
<223> OTHER INFORMATION: synthetic peptide

<400> SEQUENCE: 29

Ser Asp Trp Gly Val Leu Thr Asn Leu Gly Ile Leu Leu Leu Leu Ser
1               5                   10                  15

Ile Ala Val Leu Ile Ala Leu Ser Cys Ile Cys Gly Ser Gly Lys Lys
            20                  25                  30

Arg Thr Leu Arg Lys Asn Asp Arg Lys Lys Arg
        35                  40

<210> SEQ ID NO 30
<211> LENGTH: 43
<212> TYPE: PRT
<213> ORGANISM: Artificial Sequence
<220> FEATURE:
<223> OTHER INFORMATION: synthetic peptide

<400> SEQUENCE: 30

Arg Gln Trp Ile Pro Ala Gly Ile Gly Val Thr Gly Val Ile Ile Ala
1               5                   10                  15

Val Ile Ala Leu Phe Cys Ile Cys Lys Phe Val Gly Ser Gly Lys Lys
            20                  25                  30

Arg Thr Leu Arg Lys Asn Asp Arg Lys Lys Arg
        35                  40

<210> SEQ ID NO 31
<211> LENGTH: 43
<212> TYPE: PRT
<213> ORGANISM: Artificial Sequence
<220> FEATURE:
<223> OTHER INFORMATION: synthetic peptide

<400> SEQUENCE: 31

Arg Gln Trp Ile Pro Ala Gly Ile Gly Ile Thr Gly Ile Ile Ile Ala
1               5                   10                  15

Ile Ile Ala Leu Leu Cys Val Cys Lys Leu Leu Gly Ser Gly Lys Lys
            20                  25                  30

Arg Thr Leu Arg Lys Asn Asp Arg Lys Lys Arg
            35                  40

<210> SEQ ID NO 32
<211> LENGTH: 48
<212> TYPE: PRT
<213> ORGANISM: Artificial Sequence
<220> FEATURE:
<223> OTHER INFORMATION: synthetic peptide

<400> SEQUENCE: 32

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Gly Ser Gly Lys Lys Arg Thr Leu Arg Lys Asn Asp Arg Lys Lys Arg
            35                  40                  45

<210> SEQ ID NO 33
<211> LENGTH: 48
<212> TYPE: PRT
<213> ORGANISM: Artificial Sequence
<220> FEATURE:
<223> OTHER INFORMATION: synthetic peptide

<400> SEQUENCE: 33

Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Gly Ser Gly Lys Lys Arg Thr Leu Arg Lys Asn Asp Arg Lys Lys Arg
            35                  40                  45

<210> SEQ ID NO 34
<211> LENGTH: 34
<212> TYPE: PRT
<213> ORGANISM: Artificial Sequence
<220> FEATURE:
<223> OTHER INFORMATION: synthetic peptide

<400> SEQUENCE: 34

Met Lys Thr Thr Cys Phe Leu Ile Ser Leu Ile Leu Ile Gln Gly Thr
1               5                   10                  15

Lys Asn Gly Ser Gly Lys Lys Arg Thr Leu Arg Lys Asn Asp Arg Lys
            20                  25                  30

Lys Arg

<210> SEQ ID NO 35
<211> LENGTH: 34
<212> TYPE: PRT
<213> ORGANISM: Artificial Sequence
<220> FEATURE:
<223> OTHER INFORMATION: synthetic peptide

<400> SEQUENCE: 35

Met Lys Thr Thr Cys Leu Leu Ile Ser Leu Ile Leu Ile Gln Gly Val
1               5                   10                  15

Lys Thr Gly Ser Gly Lys Lys Arg Thr Leu Arg Lys Asn Asp Arg Lys
            20                  25                  30

Lys Arg

<210> SEQ ID NO 36
<211> LENGTH: 32
<212> TYPE: PRT
<213> ORGANISM: Artificial Sequence
<220> FEATURE:
<223> OTHER INFORMATION: synthetic peptide

<400> SEQUENCE: 36

Met Ala Ile Val Gly Ile Val Leu Leu Ile Val Val Thr Phe Leu Ala
1               5                   10                  15

Ile Lys Thr Lys Lys Arg Thr Leu Arg Lys Asn Asp Arg Lys Lys Arg
            20                  25                  30

<210> SEQ ID NO 37
<211> LENGTH: 34
<212> TYPE: PRT
<213> ORGANISM: Artificial Sequence
<220> FEATURE:
<223> OTHER INFORMATION: synthetic peptide

<400> SEQUENCE: 37

Phe Phe Phe Ile Ile Gly Leu Ile Ile Gly Leu Phe Leu Val Leu Arg
1               5                   10                  15

Val Gly Ile His Leu Lys Lys Arg Thr Leu Arg Lys Asn Asp Arg Lys
            20                  25                  30

Lys Arg

<210> SEQ ID NO 38
<211> LENGTH: 34
<212> TYPE: PRT
<213> ORGANISM: Artificial Sequence
<220> FEATURE:
<223> OTHER INFORMATION: synthetic peptide

<400> SEQUENCE: 38

Val Leu Ala Val Ile Ile Gly Phe Val Ile Leu Met Phe Leu Ile Lys
1               5                   10                  15

Leu Ile Gly Val Leu Lys Lys Arg Thr Leu Arg Lys Asn Asp Arg Lys
            20                  25                  30

Lys Arg

<210> SEQ ID NO 39
<211> LENGTH: 19
<212> TYPE: PRT
<213> ORGANISM: Artificial Sequence
<220> FEATURE:
<223> OTHER INFORMATION: synthetic peptide

<400> SEQUENCE: 39

Met Ala Ile Val Gly Ile Val Leu Leu Ile Val Val Thr Phe Leu Ala
1               5                   10                  15

Ile Lys Thr

<210> SEQ ID NO 40
<211> LENGTH: 21
<212> TYPE: PRT
<213> ORGANISM: Artificial Sequence
<220> FEATURE:
<223> OTHER INFORMATION: synthetic peptide

<400> SEQUENCE: 40

Phe Phe Phe Ile Ile Gly Leu Ile Ile Gly Leu Phe Leu Val Leu Arg

```
1               5              10              15
Val Gly Ile His Leu
            20

<210> SEQ ID NO 41
<211> LENGTH: 21
<212> TYPE: PRT
<213> ORGANISM: Artificial Sequence
<220> FEATURE:
<223> OTHER INFORMATION: synthetic peptide

<400> SEQUENCE: 41

Val Leu Ala Val Ile Ile Gly Phe Val Ile Leu Met Phe Leu Ile Lys
1               5                  10                  15

Leu Ile Gly Val Leu
            20
```